United States Patent [19]

Seckinger et al.

[11] Patent Number: 5,312,799
[45] Date of Patent: May 17, 1994

[54] AMIDES

[75] Inventors: Karl Seckinger, Riegel, Fed. Rep. of Germany; Karlheinz Milzner, Basel, Switzerland; Fred Kuhnen, Weil, Fed. Rep. of Germany; Sasank S. Mohanty, Baden, Switzerland

[73] Assignee: Sandoz Ltd., Basel, Switzerland

[21] Appl. No.: 880,424

[22] Filed: May 8, 1992

[30] Foreign Application Priority Data

May 17, 1991 [GB] United Kingdom ............... 9110693

[51] Int. Cl.$^5$ .................. A01N 43/86; A01N 43/40; C07D 211/06; C07D 207/46
[52] U.S. Cl. .................... 504/249; 504/287; 504/221; 504/224; 546/226; 548/567; 544/54; 544/58.4
[58] Field of Search ............... 546/226; 504/249, 287; 548/567

[56] References Cited

U.S. PATENT DOCUMENTS

| 5,055,450 | 10/1991 | Edwards et al. | 514/19 |
| 5,194,084 | 3/1993 | Findeisen et al. | 504/273 |
| 5,211,739 | 5/1993 | Lopez | 504/273 |

FOREIGN PATENT DOCUMENTS

| 881227 | 7/1980 | Belgium . |
| 0070389 | 1/1983 | European Pat. Off. . |
| 0221439 | 5/1987 | European Pat. Off. . |
| 0264865 | 4/1988 | European Pat. Off. . |
| 57-045105 | 3/1982 | Japan . |
| 59-048481 | 6/1984 | Japan . |
| 949729 | 2/1964 | United Kingdom . |
| 1114397 | 5/1968 | United Kingdom . |

OTHER PUBLICATIONS

C.A. 92.141802 (1980).
C.A. 87.118063x(1977).

Primary Examiner—Mukund J. Shah
Assistant Examiner—Matthew V. Grumbling
Attorney, Agent, or Firm—Allen E. Norris

[57] ABSTRACT

This invention described in this patent application relates to novel amides of the formula (I)

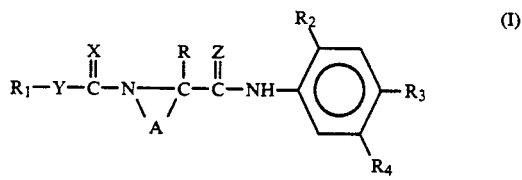

wherein the substituents are as defined in the disclosure, intermediates for such amides, synthesis thereof and their use for the control of weeds.

12 Claims, No Drawings

AMIDES

This invention relates to novel amides, intermediates therefore, synthesis thereof, and the use of said compounds for the control of More particularly, one aspect of this invention relates to a compound of the formula (I)

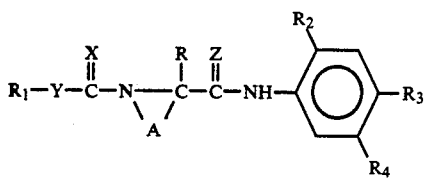

wherein

R is H, $C_{1-3}$alkyl or $C_{2-3}$alkenyl optionally substituted by halo; or is $C_{2-3}$alkinyl;

$R_1$ is phenyl($C_{1-4}$alkyl)$_n$, wherein the phenyl group is optionally substituted by one or more groups selected from $-C(O)-O-C_{1-4}$alkyl, $C_{1-8}$alkyl, $C_{1-8}$haloalkyl, halo, nitro, cyano, $-SO_2C_{1-4}$alkyl, $SO_2NR_5R_5'$ and $S(O)NR_5R_5'$; or is $C_{5-8}$cycloalkenyl; $-N=R_6$; $C_{2-8}$alkenyl, $C_{1-8}$alkyl or $C_{3-8}$alkinyl optionally substituted with one or more halo; or is $C_{1-4}$alkyl$-SO_2-C_{1-4}$alkyl;

$R_2$ is halo or hydrogen;

$R_3$ is halo, cyano or $C_{1-4}$alkyl;

$R_4$ is H; $NO_2$; $NH_2$; CN; $C_{1-8}$alkyl optionally substituted by CN; $C_{2-8}$alkenyl optionally substituted by CN; $C_{2-8}$alkinyl; ($C_{2-5}$alkoxycarbonyl)-$C_{1-4}$alkyl, whereby the carbon atom of the alkyl group alpha to the alkoxycarbonyl group may bear one more $C_{2-5}$alkoxcarbonyl groups or a cyano group; ($C_{2-5}$alkoxycarbonyl)-$C_{-4}$alkoxy-$C_{1-4}$alkyl; ($C_{2-5}$alkoxycarbonyl)-$C_{1-4}$alkylamino-$C_{1-4}$alkyl; ($C_{2-5}$alkoxycarbonyl)-$C_{2-5}$alkenyl, whereby the alkenyl moiety is optionally substituted by halogen; $C_{1-4}$alkylthio-$C_{1-4}$alkyl; $C_{1-4}$alkylsulfonyl-$C_{1-4}$alkyl; $C_{1-4}$alkoxy-$C_{1-4}$alkoxy; $X(Alk)_mR_7$; $OCH(SR_8)-COOR_9$; $NR_{10}R_{11}$; $COOR_{12}$; $CONR_{13}R_{13}'$; $COR_{14}$ or $R_{15}$;

or $R_3$ and $R_4$ join together with the phenyl ring to form a bicyclic ring containing nine to ten ring atoms, one to three of said ring atoms optionally being selected from oxygen, nitrogen and sulfur, and optionally being substituted with one or more groups selected from $C_{3-8}$alkinyl, $C_{1-8}$alkyl, halo, oxo, $C_{1-4}$alkylene-$R_{16}$, and $C_{2-8}$alkenyl;

$R_5$ and $R_5'$ independently are $C_{1-4}$alkyl;

$R_6$ is $C_{2-8}$alkylidene;

$R_7$ is H; $C_{1-4}$alkyl, $C_{2-5}$alkenyl $C_{2-5}$alkinyl, or $C_{3-8}$cycloalkyl, which hydrocarbyl is unsubstituted or substituted by one or more halogen or by CN; cyclopentanonyl; phenyl optionally substituted by O—Alk'—$COOR_8$; or is $C_{2-5}$alkanoyl; $C_{2-5}$alkoxycarbonyl; $C_{2-8}$(alkoxycarbonyl)($C_{3-8}$cycloalkyloxy)carbonyl, in which the alkoxy or cycloalkyloxy group is optionally substituted by one or more halo; $CONR_9R_8'$, $C(=NOR_8)-COOR_8'$, CN; $P(O)(OR_8)(OR_8')$ or $R_{15}$;

$R_8$ and $R_8'$, independently are $C_{1-4}$alkyl;

$R_9$ is $C_{1-4}$alkyl optionally substituted by one or more halo;

$R_{10}$ is H or $C_{1-4}$alkyl;

$R_{11}$ is H; $C_{1-4}$alkyl, optionally substituted by $P(O)(OR_8)(R_8')$; $C_{2-5}$alkanoyl; $C_{2-5}$alkoxycarbonyl; or $C_{2-5}$alkoxycarbonyl-$C_{1-4}$alkyl;

$R_{12}$ is $N=(C_{2-8}$alkylidene); $C_{1-4}$alkyl optionally substituted by one or more groups selected from halo, $C_{1-4}$alkoxy, tri-$C_{1-4}$alkylsilyloxy, tri-$C_{1-4}$alkyl-silyl, (tri-$C_{1-4}$alkylsilyloxy)-carbonyl, $C_{2-5}$alkoxycarbonyl, $P(O)(OR_8)(OR_8')$, $C_{2-5}$alkanoyl-oxy or by di($C_{1-4}$alkylamino)-carbonyloxy in which both alkyl groups may be tied together to form a saturated 5 to 6 membered heteroring optionally containing one further heteroatom selected from O, S and N, and in which any further N-heteroatom present may, depending on the hydrogenation degree of the heteroring, bear a hydrogen or a $C_{1-4}$alkyl group;

$R_{13}$ is H or $C_{1-4}$alkyl;

$R_{13}'$ is H, $C_{1-4}$alkyl optionally substituted by halo, $C_{1-4}$alkoxy, phenyl, CHO, $C_{2-5}$alkanoyl, $C_{1-4}$alkylsulfonyl, ($C_{2-5}$alkoxycarbonyl)-$C_{1-4}$alkyl or($C_{2-5}$alkoxycarbonyl)-$C_{1-4}$alkoxy;

or $R_{13}$ and $R_{13}'$ together form a 4 to 6 membered heteroring optionally containing one or two further heteroatoms selected from O, S and N, whereby, depending on the hydrogenation degree of the heteroring, any further N-heteroatom may bear hydrogen or be substituted by $C_{1-4}$alkyl;

$R_{14}$ is H or $C_{1-4}$alkyl;

$R_{15}$ is a heterocyclic ring having 5 or 6 ring atoms, one to three of said ring atom being selected from oxygen, sulfur and nitrogen, which ring is optionally substituted with one or more $C_{1-4}$alkyl groups;

$R_{16}$ is CN; $COOR_{12}$; $OC_{1-4}$alkyl; or is 4-tetrahydropyranyl, 2H-5,6-dihydro-thiin-3-yl, 2-pyridyl, 2-pyrazinyl, 1,2-oxazol-3-yl, or 1,2,4-oxdiazol-3-yl, each of which is optionally substituted with $C_{1-4}$alkyl;

Alk and Alk' independently are $C_{1-4}$alkylene;

n and m independently are 0 or 1;

A is a $C_{3-4}$alkylene or $C_{3-4}$alkenylene straight chain optionally substituted by one to three halogen; or is a propylene or propenylene straight chain interposed by a heteroatom or heterogroup selected from S, O, SO, $SO_2$, and $NR_{10}$; and X, Y and Z are independently selected from O and S.

Where $R_1$ is or contains a $C_{1-8}$alkyl group or $R_4$ is a $C_{1-8}$alkyl group, it is preferably a $C_{1-4}$ alkyl group. Any alkyl group may be branched or straight chain.

Where $R_1$ is a $C_{2-8}$alkenyl group, it is preferably a $C_{2-5}$alkenyl group. Any alkenyl group may be either branched or straight chain.

Where the bicyclic ring formed by junction of $R_3$ and $R_4$ is substituted by a $C_{3-8}$alkinyl group, it is preferably a $C_{3-5}$alkinyl group. Any alkinyl groups may be either branched or straight chain.

Where $R_1$ is a $C_{5-8}$cycloalkenyl group, it is preferably a $C_{5-6}$cycloalkenyl group.

Where $R_7$ contains a $C_{3-8}$CYcloalkyl group, it is preferably a $C_{3-5}$ cycloalkyl group.

Where $R_1$, $R_4$, $R_7$ or $R_2$ contains halogen, it is preferably chlorine or fluorine.

$R_6$ may be straight or branched chain; it may be cyclic or contain a cycloalkyl group.

Where $R_6$ cycloalkylidene, it is preferably $C_{3-6}$cloalkylidine, more preferably $C_{2-6}$cycloalkylidene.

Where $R_6$ is branched or straight chain alkylidene it is preferably $C_{2-8}$alkylidene, more preferably $C_{2-5}$alkylidene.

Where $R_3$ and $R_4$ join together with the phenyl ring to form a bicyclic ring, it is preferably an indanone; a benzazinone, particularly a quinolinone; a benzoxazinone; a benzodiazinone particularly dihydroquinoxalinone; a benzothiazinone; a benzodioxane; a benzopyrane; a benzopyrone, particularly coumarin; a benzazole, particularly an indole, an indolone, an indazole, a benzotriazole, an isatine or a benzimidazolone; a benzoxazolone; a benzothiazolone; a benzofurane; or a benzdioxolane;

Where $R_1$, $R_4$, $R_7$, $R_9$, $R_{12}$, $R_{15}$ or A are substituted, they are preferably mono-, di- or tri-substituted.

X, Y and Z are preferably oxygen.

R is preferably H.

$R_1$ is preferably selected from phenyl optionally substituted with halogen, nitro or $CH_3OC(O)$—; $C_{1-4}$alkyl optionally substituted with one to four halogen atoms; $C_{2-4}$alkenyl; or $C_{2-3}$alkylidene=N—.

$R_2$ is preferably chlorine or fluorine, more preferably fluorine.

$R_3$ is preferably CN, Br, Cl or methyl.

$R_4$ is preferably $O(Alk)_mR_7$, $COOR_{12}$ or $CONR_{13}R_3'$;

$R_7$ is preferably $C_{1-4}$alkyl, $C_{2-5}$alkenyl, $C_{2-5}$alkinyl, or $C_{2-5}$alkoxycarbonyl.

$R_{12}$ is preferably $C_{1-4}$alkyl optionally substituted by halo.

$R_{13}$ is preferably H.

$R_{13}'$ is preferably $C_{1-4}$alkyl optionally substituted by halo.

$R_{15}$ is preferably an azole particularly pyrazol, triazol or benzimidazol; thiophene; furane; oxadiazole; oxazoline; dioxolane; dithiolane; pyrane; or dihydro- or tetrahydrothiine; and is preferably a heteroring containing 1-3 heteroatoms.

A is preferably straight chain butylene substituted by fluorine.

Alk is preferably $CH_2$ or $CH(CH_3)$;

Compounds of the formula (I) may be prepared by reacting a compound of the formula (II)

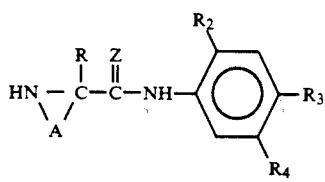   (II)

with a compound of the formula (III)

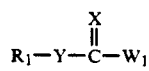   (III)

wherein R—$R_4$, A, X, Y and Z are as previously defined and $W_1$ is halogen.

This reaction is suitably carried out at 0°-50° C. in an inert solvent such as methylene chloride, chloroform, acetone, acetonitrile or ether in the presence of a base such as triethylamine, sodium carbonate or potassium carbonate. The compound of the formula (I) may be recovered from solution by standard techniques, such as liquid-liquid phase separation, and subsequent evaporation in vacuo.

Compounds of the formula (II) are believed to be novel, and form another aspect of this invention.

Compounds of the formula (II) can be prepared by reacting a compound of the formula (IV)

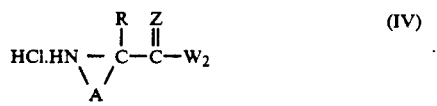   (IV)

with a compound of the formula (V)

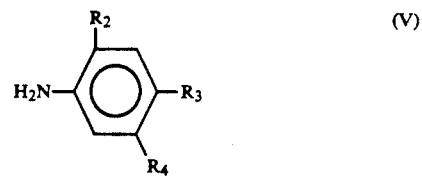   (V)

wherein A, Z, R and $R_{2-4}$ are as previoiusly defined and $W_2$ is halogen.

This reaction is exothermic and is suitably carried out at 0°-500° C. in an inert solvent as previously mentioned. After the reaction subsides, a suitable base, as previously mentioned, is added, after which the reaction mixture is stirred. The compound of the formula (II) may be recovered from solution by standard techniques, such as liquid-liquid phase separation, and subsequent evaporation in vacuo.

Compounds of the formulae (III), (IV) and (V) are known, or can be prepared according standard techniques from known compounds.

The compounds of formula (I) are useful because they control the growth of plants. By plants it is meant germinating seeds, merging seedlings and established vegetation including underground portions. In particular, the compounds are useful as herbicides as indicated by causing damage to both monocotyledoneous and dicotyledoneous plants in various standard evaluations for determining such effects. The herbicidal effects are exhibited both pre- and post-emergence the plants. Such herbicidal effects indicate that the compounds of formula (I) are particularly of interest in combatting weeds (unwanted plants).

The compounds of the formula (I) are indicated mainly to be stronger acting against dicotyledoneous plants than monocotyledoneous plants. Relatively less toxicity towards crops than towards weeds is further indicated. Hence, the compounds are of particular interest as selective herbicides to combat weeds in a crop locus, particularly as locus of a crop such as, for example, sugarbeet, sunflower, cotton soybean, corn and wheat.

The present invention therefore also provides a method of combatting weeds in a locus which comprises applying to the weeds or their locus a herbicidally effective amount of a compound of the invention. When selective action is desired in crop locus, the amount applied will be sufficient to combat weeds without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation in application, the various conditions of treatment such as soil and weather and the like. However, in general, satisfactory results in weed control are usually obtained upon application of the compounds of the invention at a rate in the range of from 0.01 to 10 kg/hectare, more usually 0.05 to 2 kg/hectare, and preferably 0.1 to 1 kg/hectare, the application being repeated as necessary. When used in crops, the application usually will not exceed about 5 kg/hectare, and is usually in the range of 0.01 to 1 kg/hectare.

For practical use as herbicides, the compounds of formula (I) may be and are preferably employed in herbicidal compositions comprising a herbicidal effective amount of the compound and an inert carier which is agriculturally acceptable in the sense of not, by reason of its presence, poisoning the agricultural environment including the immediate soil of application or any crops present therein or otherwise being unsafe for application. Such compositions of formulations may contain 0.01% to 99% by weight of active ingredient, from 0 to 20% by weight of agriculturally acceptable surfactants and 1 to 99.99% by weight of the inert carrier. Higher ratios of surfactant to active ingredient are sometimes desirable and are achieved by incorporation into the formulation or by tank mixing. Application forms of composition typically contain between 0.01 and 25% by weight of active ingredient, but lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained by conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compound with a solid inert carrier such as talc, clay, silica and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Alternatively, the compounds of the invention may be used in micro-encapsulated form.

Agriculturally acceptable additives may be employed in the herbicidal compositions to improve the performance of the active ingredient and to reduce foaming, caking and corrosion. Surfactant as used herein means agriculturally acceptable material which imparts emulsifiability, spreading, wetting, dispersiblity or other surface-modifying properties properties. Examples of surfactants are sodium lignin sulphonate and lauryl sulphate.

Carriers as used herein mean a liquid or solid material used to dilute a concentrated material to a usable or desirable strength. For dusts or granules it can be e.g. talc, kaolin or diatomaeous earth, for liquid concentrate forms, a hydrocarbon such as xylene or an alcohol such as isopropanol; and for liquid application forms, e.g. water or diesel oil.

The compositions of this application can also comprise other compounds having biological activity, e.g. compounds having similar or complementary herbicidal ativity or compounds having antidotal, fungicidal or insecticidal activity.

Typical herbicidal composition, according to this invention, are illustrated by the following Examples A, B and C in which the quantities are in parts by weight.

EXAMPLE A

Preparation of a Dust

10 Parts of a compound of formula (I) and 90 parts of powdered talc are mixed in a mechanical grinder-blender and are ground until a homogeneous, free-flowing dust of the desired particle size is obtained. This dust is suitable for direct application to the site of the weed infestation.

EXAMPLE B

Preparation of Wettable Powder

25 Parts of a compound of formula (I) are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13.37 Parts of a compound are mixed in a beaker with 1.43 parts of Toximul 360A (a mixture of anionic and non-ionic surfactants containing largely anionic surfctants), 5.61 parts of Toximul 360A (a mixture of anionic and non-ionic surfactants containing largely non-ionic surfactants), 23.79 parts of dimethylformamide and 55.8 parts of Tenneco 500–100 (predominantly a mixture of alkylated aromatics such as xylene and ethylbenzene) until solution is effected. The resulting EC is diluted with water for use.

FINAL COMPOUNDS

EXAMPLE 1—1

2[[(4-chloro-2-fluoro-5-isopropoxyphenyl)amino]carbonyl]-1-piperidine carboxylic acid-phenylester To 15.6 g (0.05 mol) pipecolic acid 4-chloro-2-fluoro 5-isopropoxy anilide dissolved in 250 ml methylenchloride are added 5.5 g (0.054 mol) triethylamine. 7.8 g (0.05 mol) of phenylchloroformate are added dropwise and the reaction mixture is stirred for 15 minutes at room temperature. 100 ml water is added and the organic layer is separated, washed with additional 100 ml water, dried (MgSO$_4$) and evaporated in vacuo. The residue is homogenous by TLC (Rf=0.76 CH$_2$—CH$_2$/CH$_3$OH, 98:2)

In an analogous manner, the following compounds of formula (Ia) set forth in Table 1 are made.

TABLE 1

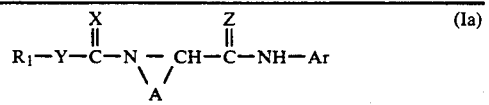

For compounds 1-2 through 1-184 and 221 through 227 Ar is 2-R$_2$-4-R$_3$O5-R$_4$-phenyl.

For compounds 1-185 through 1-220, Ar is as indicated.

The orientation of the alkylene or alkenylene chain "A" set forth below is such that the first carbon in the chain is bound to the nitrogen in formula (Ia).

| Compd. | R₁ | A | X | Y | Z | R₂ | R₃ | R₄ | mp °C. or $R_f$ (silica gel) |
|---|---|---|---|---|---|---|---|---|---|
| 1-2 | phenyl | —(CH₂)₄— | O | O | O | F | Cl | OCH₂C≡CH | 130° C. |
| 1-3 | " | " | " | " | " | " | " | H | 82° C. |
| 1-4 | " | " | " | " | " | " | " | OCH₃ | $R_f$ = 0,25 (CH₂Cl₂) |
| 1-5 | " | " | " | " | " | " | " | OCH₂CH₃ | $R_f$ = 0,67(CH₂Cl₂/CH₃OH, 98:2) |
| 1-6 | " | " | " | " | " | " | " | OCOOCH₃ | $R_f$ = 0,75 (Acetone) |
| 1-7 | " | " | " | " | " | " | " | OCH₂—CH₂—CH₃ | $R_f$ = 0,65 (CH₂Cl₂/CH₃OH, 98:2) |
| 1-8 | CH₃CH₂— | " | " | " | " | " | " | H | 67° C. |
| 1-9 | " | " | " | " | " | " | " | OCH₃ | $R_f$ = 0,13 (CH₂Cl₂) |
| 1-10 | benzyl | " | " | " | " | " | " | OCH(CH₃)₂ | $R_f$ = 0,55 (CH₂Cl₂/CH₃OH, 98:2) |
| 1-11 | " | " | " | " | " | " | " | OCH₃ | $R_f$ = 0,35 (CH₂Cl₂) |
| 1-12 | CH₃— | " | " | " | " | " | " | OCH(CH₃)₂ | 118° C. |
| 1-13 | " | —CH=CHSCH₂— | " | " | " | " | " | OCH(CH₃)₂ | 92° C. |
| 1-14 | " | " | " | " | " | " | " | " | |
| 1-15 | CH₃OCO-phenyl | " | " | " | " | " | " | OCH₂CH₂CH₃ | $R_f$ = 0,54 (CH₂Cl₂/CH₃OH, 98:2) |
| 1-16 | CH₃OCO-phenyl | " | " | " | " | " | " | OCH₂CH₃ | $R_f$ = 0,59 (CH₂Cl₂/CH₃OH, 98:2) |
| 1-17 | CH₃OCO-phenyl | —(CH₂)₄— | " | " | " | " | " | OH(CH₃)₂ | $R_f$ = 0,56 (CH₂Cl₂/CH₃OH, 98:2) |
| 1-18 | phenyl | " | O | " | " | " | " | OCH₂CH₂CH₃ | 103° C. |
| 1-19 | " | " | S | " | " | " | " | OCH(CH₃)₂ | 105° C. |
| 1-20 | 4-CH₃-phenyl | " | " | " | " | " | " | OCH(CH₃)₂ | 100° C. |
| 1-21 | " | " | " | " | " | " | " | OCH(CH₃)₂ | $R_f$ = 0,72 (CH₂Cl₂/CH₃OH, 98:2) |
| 1-22 | 4-Cl-phenyl | " | " | S | " | " | " | OCH(CH₃)₂ | 135° C. |
| 1-23 | " | " | O | O | " | " | " | OCH(CH₃)₂ | $R_f$ = 0,64 (CH₂Cl₂/CH₃OH, 98:2) |
| 1-24 | " | " | " | " | " | " | " | OCH(CH₃)₂ | $R_f$ = 0,60 (CH₂Cl₂/CH₃OH, 98:2) |
| 1-25 | CH₂=CH—CH₂— | " | " | " | " | " | " | " | $R_f$ = 0,69 (Acetone) |
| 1-26 | (CH₃)₂CH—CHCl— | " | " | " | " | " | " | " | $R_f$ = 0,18 (CH₂Cl₂) |
| 1-27 | Cl₃C—CHCl | " | " | " | " | " | " | " | 55° C. |
| 1-28 | CH₂=CH— | " | " | " | " | " | " | " | 92° C. |
| 1-29 | (CH₃)₂C=N | " | " | " | " | " | " | " | 56° C. |
| 1-30 | (CH₃)₂C=N— | —(CH₂)₄ | " | " | " | " | " | OC₃H₉-cycl. | 154° |
| 1-31 | phenyl | " | " | " | " | " | " | NH₂ | $R_f$ = 0,42 (ethyl acetate, hereinafter Est/Hex, 1:1) |
| 1-32 | " | " | " | " | " | F | " | F | 52° C. |
| 1-33 | " | " | " | " | " | " | Cl | I | 93° C. |
| 1-34 | " | " | " | " | " | " | " | OCCH₃ | $R_f$ = 0,45 (Est/Hex, 1:1) |
| 1-35 | " | " | " | " | " | " | " | OCH(CH₃)₂ | 105–105°; $R_f$ = 0,54 (Et₂O) |
| 1-36 | CH₃— | —(CH₂)₂—SCH₂— | " | " | " | " | " | " | 83–84°; $R_f$ = 0,44 (Et₂O) |
| 1-37 | " | " | " | " | " | " | " | " | $R_f$ = 0,38 (Est-Hex 1:1) |
| 1-38 | (CH₃)₂C=N | —(CH₂)₄ | " | " | " | " | " | OCH(CH₃)≡CH | 127° |
| 1-39 | 4-Cl-phenyl | —CH₂CH=CHCH₂— | " | " | " | " | " | OC₄H₉-sec | 93–95° |
| 1-40 | 4-NO₂-phenyl | —(CH₂)₃ | " | " | " | " | " | OCH(CH₃)₂ | 142°C. |
| 1-41 | 4-Cl-phenyl | " | " | " | " | " | " | OC₂≡CH | 144° C. |
| 1-42 | phenyl | " | " | " | " | " | " | " | 132° C. |
| 1-43 | " | " | " | " | " | " | " | O—CO—OCH₃ | 63° C. |
| 1-44 | " | —(CH₂)₂—SCH₂— | " | " | " | " | " | OCH₃ | 121° |
| 1-45 | " | " | " | " | " | " | " | OC₂H₅ | $R_f$ = 0,49 (Est/Hex 1:1) |
| 1-46 | " | " | " | " | " | " | " | OC₃H₇-n | $R_f$ = 0,51 (Est/Hex 1:1) |
| 1-47 | 4-Cl-phenyl | —(CH₂)₂CH(F)(CH₂)— | O | O | O | F | Cl | OCHCH₃—C≡CH | |
| 1-48 | " | " | " | " | " | " | " | OCH(CH₃)₂ | |
| 1-49 | " | —(CH₂)₄— | " | " | " | " | " | OCH₂-phenyl | |
| 1-50 | " | " | " | " | " | " | " | OCHCH₃)phenyl | |
| 1-51 | " | " | " | " | " | " | " | OCHCH₃—CH₂OCH₃ | |
| 1-52 | " | " | " | " | " | " | " | OCH₂COCH₃ | |

-continued

| | | | | | | |
|---|---|---|---|---|---|---|
| 1-53 | " | " | " | " | " | OCH$_2$CH=CH$_2$ |
| 1-54 | " | " | " | " | " | OCH$_2$CH=CH—Cl |
| 1-55 | " | " | " | " | " | OCH$_2$CCl=CH$_2$ |
| 1-56 | " | " | " | " | " | OCH$_2$-(2,2-di-Cl-cyclopropyl) |
| 1-57 | " | " | " | " | " | OCH$_2$-(2-Cl-cyclopropyl) |
| 1-58 | phenyl | —(CH$_2$)$_2$—SCH$_2$— | " | " | " | OCH$_2$-cyclopropyl |
| 1-59 | " | " | " | " | " | OC$_4$H$_9$-sec |
| 1-60 | " | " | " | " | " | OC$_4$H$_9$-cycl | R$_f$ = 0.56 (Est/Hex 1:1) |
| 1-61 | " | " | " | " | " | OCH$_2$C≡CH | 134–135° |
| 1-62 | " | " | " | " | " | OCH(CH$_3$)C≡CH | 131–132° |
| 1-63 | 4-Cl-phenyl | —(CH$_2$)$_4$— | O | O | O | OCH$_2$CH$_2$OCH$_2$CH$_3$ | R$_f$ 0.27 (Est/Hex 1:3) |
| 1-64 | " | " | " | " | " | OCH$_2$-(2-tetrahydrofuryl) |
| 1-65 | " | " | " | " | " | OCH$_2$-(2-tetrahydropyranyl) |
| 1-66 | " | " | " | " | " | OCH$_2$-(2H-5,6-dihydrothiin-3-yl) |
| 1-67 | " | " | " | " | " | OCHCH$_3$—COOEt |
| 1-68 | " | " | " | " | " | OCH$_2$CN |
| 1-69 | " | " | " | " | " | OCH$_2$—C(=NOCH$_3$)—COOC$_2$H$_5$ |
| 1-70 | " | " | " | " | " | OCH$_2$-(1,3-dioxolan-2-yl) |
| 1-71 | " | " | " | " | " | OCH$_2$-(1,3-dithiolan-2-yl) |
| 1-72 | " | " | " | " | " | OCH$_2$—CO-(1,4-oxazin-4-yl) |
| 1-73 | " | —(CH$_2$)$_2$CH(F)CH$_2$— | " | " | " | OCH$_2$COOC$_5$H$_{11}$-n |
| 1-74 | " | —(CH$_2$)$_4$— | " | " | " | O-(2-oxo-cyclopentyl) |
| 1-75 | " | " | " | " | " | OPO(OCH$_3$)$_2$ |
| 1-76 | CH$_2$=CH—CH$_3$ | —(CH$_2$)$_2$CH(F)CH$_2$— | " | " | " | OCH(CH$_3$)C≡CH |
| 1-77 | " | —(CH$_2$)$_4$— | " | " | " | OCH$_2$CH=CH$_2$ |
| 1-78 | 4-Cl-phenyl | " | " | " | " | OCHCH$_3$—COOCH$_2$CH$_3$ |
| 1-79 | " | " | " | " | " | OCH—(SCH$_3$)COOCH$_2$CH$_2$Cl |
| 1-80 | 4-Cl-phenyl | —(CH$_2$)$_4$— | O | O | F | O—CH$_2$P(OCH$_2$CH$_3$)$_2$ ‖ O |
| 1-81 | phenyl | —(CH$_2$)$_2$CH(F)CH$_2$— | " | " | " | OCH$_2$CF$_3$ |
| 1-82 | " | —(CH$_2$)$_4$— | " | " | " | OCHF$_2$ |
| 1-83 | " | " | " | " | " | OCH$_2$COO(cyclopentyl) |
| 1-84 | " | " | " | " | " | OCH$_2$-(1-pyrazolyl) |
| 1-85 | " | " | " | " | " | 4-[C$_2$H$_5$OOC—CH(CH$_3$)—O]-phenoxy |
| 1-86 | " | " | " | " | " | OCH$_2$-(2-thienyl) |
| 1-87 | 4-Cl-phenyl | " | " | " | Cl | OCH(CH$_3$)-(3-CH$_3$-1,2,4-oxadiazol-5-yl) |
| 1-88 | " | —(CH$_2$)$_2$CH(F)CH$_2$— | " | " | H | OCH(CH$_3$)$_2$ |
| 1-89 | " | —(CH$_2$)$_4$— | " | " | F | " |
| 1-90 | " | " | " | " | CH$_3$ | " |
| 1-91 | " | " | " | " | CN | " |
| 1-92 | " | —(CH$_2$)$_2$CH(F)CH$_2$— | " | " | CN | " |
| 1-93 | " | —(CH$_2$)$_4$— | " | " | Cl | OCH$_2$C≡CH |
| 1-94 | " | " | " | " | " | SCH(CH$_3$)$_2$ |
| 1-95 | " | " | " | " | " | SCH$_2$C≡CH |
| 1-96 | 4-Cl-phenyl | " | O | O | F | SCH$_2$COOCH$_2$CH$_3$ |
| 1-97 | " | " | " | " | Cl | SCH(CH$_3$)COOCH$_2$CH$_3$ |
| 1-98 | " | " | " | " | " | SCH$_2$-phenyl |
| 1-99 | " | " | " | " | " | S-(tetrahydro-2-pyranyl) NHCH$_2$COOCH$_2$CH$_3$ |

-continued

| | | | | | | |
|---|---|---|---|---|---|---|
| 1-100 | " | " | " | " | " | N(CH₃)₂ |
| 1-101 | " | " | " | " | " | NCH₃—COOCH₂CH₃ |
| 1-102 | " | " | " | " | " | NHCOCH(CH₃)CH₂CH₃ |
| 1-103 | " | " | " | " | " | NHCH(C₂H₅)—P(O)(C₂H₅)(OC₂H₅) |
| 1-104 | CH₂=CH—CH₃ | " | " | " | " | S—CH(CH₃)₂ |
| 1-105 | 4-Cl-phenyl | " | " | " | " | COOCH(CH₃)₂ |
| 1-106 | —(CH₂)₂CH(F)CH₂— | " | " | " | " | " |
| 1-107 | —(CH₂)₂CF₂CH₂— | " | " | " | " | " |
| 1-108 | " | " | " | " | " | COOCH(CH₂—F)₂ |
| 1-109 | " | " | " | " | " | COOCH₂CH₂OCH₃ |
| 1-110 | " | " | " | " | " | COON=C(CH₃)₂ |
| 1-111 | " | " | " | " | " | COOCH₂CH₂-F |
| 1-112 | 4-Cl-phenyl | —(CH₂)₄— | O | " | F | COOCH₂CH₂OSi(CH₃)₃ |
| 1-113 | " | —(CH₂)₄— | O | " | Cl | COOCH₂COOSi(CH₃)₃ |
| 1-114 | " | " | " | " | " | COOCH₂Si(CH₃)₃ |
| 1-115 | " | " | " | " | " | COOCH₂—CH₂Si(CH₃)₃ |
| 1-116 | " | " | " | " | " | COOCH₂CH₂PO(OCH₃)₂ |
| 1-117 | " | " | " | " | " | COOCH(CH₂CH₃)—PO(OCH₃)₂ |
| 1-118 | " | " | " | " | " | COOCH(CH₃)COOCH₂CH₃ |
| 1-119 | " | " | " | " | " | COOCH₂OCOCH₃ |
| 1-120 | " | " | " | " | " | COOCH(CH₃)OCO-piperidin-1-yl |
| 1-121 | " | " | " | " | " | CON(CH₃)₂ |
| 1-122 | " | " | " | " | " | CONCH₃—OCH₃ |
| 1-123 | " | " | " | " | " | CONHSO₂CH₃ |
| 1-124 | " | " | " | " | " | CONHOCH₂COOEt |
| 1-125 | " | " | " | " | " | CONHCH₂COOEt |
| 1-126 | " | " | " | " | " | CN |
| 1-127 | " | " | " | " | " | CHO |
| 1-128 | " | " | " | " | " | COCH₃ |
| 1-129 | " | " | " | " | " | 4-COOC₂H₅-1,3-dioxolan-2-yl |
| 1-130 | 4-Cl-phenyl | —(CH₂)₄— | O | " | F | 2-CH₃-1,3-dioxolan-2-yl |
| 1-131 | " | " | " | " | Cl | 4,4-di(CH₃)-4,5-dihydro-1,3-oxazol-2-yl |
| 1-132 | " | " | " | " | " | COO—CHCH₃—CH₂CH₃ |
| 1-133 | " | " | " | " | " | CH₃ |
| 1-134 | " | " | " | " | " | CH₂CH(CH₃)₂ |
| 1-135 | " | " | " | " | " | CH₂COOCH₂CH₃ |
| 1-136 | " | " | " | " | " | CH₂C(CN)(CH₃)COOC₂H₅ |
| 1-137 | " | " | " | " | " | CH₂C(CH₃)(COOC₂H₅)₂ |
| 1-138 | " | " | " | " | " | CH₂OCH₃ |
| 1-139 | " | " | " | " | " | CH₂OCH₂COOEt |
| 1-140 | " | " | " | " | " | CH₂NHCH₂COOEt |
| 1-141 | " | " | " | " | " | CH₂CH₂CN |
| 1-142 | " | " | " | " | " | CH₂CH₂COOCH₃ |
| 1-143 | " | " | " | " | " | CH₃CH(CH₃)—COOEt |
| 1-144 | " | " | " | " | " | CH=CH—CN |
| 1-145 | " | " | " | " | " | CH=CH—COOCH₃ |
| 1-146 | 4-Cl-phenyl | —(CH₂)₄— | O | " | F | CH=CBr—COOCH₃ |
| 1-147 | " | —(CH₂)₂CH(F)CH₂— | " | " | Cl | CH=CH—COOCH₃ |
| 1-148 | " | " | " | " | " | CH=C(CH₃)—CH₂COOCH₃ |
| 1-149 | 4-Cl-phenyl | —(CH₂)₄— | O | " | CN | CH₂SCH₃ |
| 1-150 | " | " | " | " | Cl | CH₂CO₂CH₃ |
| 1-151 | 4-CN-phenyl | —(CH₂)₂CH(F)CH₂— | " | " | " | OCH(CH₃)₂ |

-continued

| Compd. | R₁ | A | X | Y | Z | Ar |
|---|---|---|---|---|---|---|
| 1-152 | 4-CH₃SO₂-phenyl | | | | | |
| 1-153 | 4-CF₃-phenyl | " | | | | |
| 1-154 | 3,4-Cl₂-phenyl | " | | | | |
| 1-155 | 4-(CH₃)₂NSO₂-phenyl | " | | | | |
| 1-156 | 4-F-phenyl | " | | | | |
| 1-157 | (CH₃)₂NCO-phenyl | " | | | | |
| 1-158 | 1-cyclohexenyl | " | | | | |
| 1-159 | (CH₂)₄=N— | " | | | | |
| 1-160 | (CH₂)₅=N— | " | | | | |
| 1-161 | 4-Cl-phenyl | —CH₂CH(F)CH(F)CH₂— | | | | |
| 1-162 | " | " | | | | OCH₃ |
| 1-163 | 4-Cl-phenyl | —CH₂CH(F)CH(F)CH₂— | O | O | O | OCHCH₃C≡CH |
| 1-164 | " | " | O | O | O | OCH₂C≡CH |
| 1-165 | CH=CHCH₂— | " | O | F | Cl | OCH(CH₃)₂ |
| 1-166 | CH₂=CH— | " | | | | |
| 1-167 | 4-CH₃OCO-phenyl | CH₂CH(F)(CH₂)₂— | | | | |
| 1-168 | Cl₃C—CHCl— | " | | | | |
| 1-169 | CH₂=CCH₃— | (CH₂)₄ | | | | |
| 1-170 | —CH₂CH₂SO₂CH₃ | " | | | | |
| 1-171 | —CH₂CCl₃ | " | | | | |
| 1-172 | Cl₃C—C(CH₃)₂— | —CH₂CF₂(CF₂)₂— | | | | OCH(CH₃)₂ |
| 1-173 | ClCH₂CH₂— | —CH=CH—SCH₂— | | | | |
| 1-174 | 4-Cl-phenyl | —(CH₂)₂CH(F)— | | | | |
| 1-175 | " | —(CH₂)₂O—CH₂— | | | | |
| 1-176 | " | (CH₂)₂N(CH₃)CH₂ | | | | |
| 1-177 | " | —CH₂CF=CH—CH₂— | | | | |
| 1-178 | " | " | | | | |
| 1-179 | " | " | | | | |
| 1-180 | " | " | | | | |
| 1-181 | 4-Cl-phenyl | —CH₂CF=CH—CH₂— | O | O | O | OCH₂C≡CH |
| 1-182 | phenyl | CH₂CH=CFCH₂ | | | | OCH₃ |
| 1-183 | CH₂—CH— | CH₂CF=CFCH₂ | | | | OCH(CH₃)₂ |
| 1-184 | phenyl | " | | | | |
| 1-221 | " | (CH₂)₂CHFCH₂ | | | | F |
| 1-222 | " | " | | | | Br |
| 1-223 | " | " | | | | CN COOCH(CH₃)₂ |
| 1-224 | " | " | | | | CN OCH(CH₃)₂ |
| 1-225 | " | " | | | | CH₃ COOCH(CH₃)₂ |
| 1-226 | " | " | | | | CH₃ OCH(CH₃)₂ |
| 1-227 | " | " | | | | Cl COOCH(CH₃)₂ |

| Compd. | R₁ | A | X | Y | Z | Ar |
|---|---|---|---|---|---|---|
| 1-185 | 4-Cl-phenyl | (CH₂)₄— | O | O | O | 1-(2-propinyl)-5-F-benzo[d]pyrazol-6-yl |
| 1-186 | " | " | " | " | " | 4-CH₃-7-F-benzo[e]-1,3-dioxine-6-yl |
| 1-187 | " | " | " | " | " | 2,2,5-tri-F-benzo[d]dioxole-6-yl |
| 1-188 | " | " | " | " | " | 6-F-2,3-dihydro-benzo[b]-1,4-dioxin-7-yl |
| 1-189 | " | " | " | " | " | 4-(2-propinyl)-7-F-benzo[b]-1,4-thiazin-3-on-6-yl |
| 1-190 | " | —(CH₂)₂CH(F)CH₂— | " | " | " | 4-(2-propinyl)-7-F-Ar₁ |
| 1-191 | " | —(CH₂)₄— | " | " | " | 4-allyl-7-F-Ar₁ |
| 1-192 | " | —(CH₂)₂CH(F)CH₂ | " | " | " | 4-CH₃-7-F-Ar₁ |
| 1-193 | " | (CH₂)₄ | " | " | " | 4-(C₂H₅OOC—CH₂)-7-F-Ar₁ |
| 1-194 | " | " | " | " | " | 4-(CH₂OCH₃)-7-F-Ar₁ |
| 1-195 | " | " | " | " | " | 4-(CNCH₂)-7-F-Ar₁ |

-continued

| | | |
|---|---|---|
| 1-196 | " | 4-CH₂-(tetrahydropyran-4-yl)-7-F-Ar₁ |
| 1-197 | " | 4-CH₂-(5,6-dihydro-2H-thiin-3-yl)-7-F-Ar₁ |
| 1-198 | " | 4-CH₂(2-pyridyl)-7-F-Ar₁ |
| 1-199 | " | 4-(pyrazin-2-yl-methyl)-7-F-Ar₁ |
| 1-200 | " | 4-(1,2-oxazole-3-yl-methyl)-7-F-Ar₁ |
| 1-201 | " | 4-(5-CH₃-1,2,4-oxdiazol-3-yl-methyl)-7-F-Ar₁ |
| 1-202 | 4-Cl-phenyl | 1-(2-propinyl-6-F-Ar₂ |
| 1-203 | " | 1-allyl-6-F-Ar₂ |
| 1-204 | —(CH₂)₄— | 1-(2-propinyl)-6-F-Ar₃ |
| 1-205 | —(CH₂)₂CHFCH₂— | 1-allyl-6-F-Ar₃ |
| 1-206 | " | 1-allyl-6-F-quinoline-2(1H)-on-7-yl |
| 1-207 | " | 3-(2-propinyl)-6-F-benzo[d]-1,3-oxazole-2(3H)-on-5-yl |
| 1-208 | —(CH₂)₄— | 3-(2-pyridyl-CH₂)-6-F-Ar₄ |
| 1-209 | " | 3-(1,2-oxazole-3-yl-CH₂)-6-F-Ar₄ |
| 1-210 | " | 5-F-1-CH₃indol-6-yl |
| 1-211 | " | 6-F-chroman-7-yl |
| 1-212 | " | 5-F-2,3-dihydrobenzo[b]furan-6-yl |
| 1-213 | " | 5-F-indan-1-on-6-yl |
| 1-214 | " | 7-F-4-isopropyl-chromen-2-on-6-yl |
| 1-215 | " | 5-F-1-(2-propinyl)-1-H-indol-2,3-dion-6-yl |
| 1-216 | " | 5-F-benzo[d]imidazol-2(1H,3H)-on-6-yl |
| 1-217 | " | 5-F,1,3-di(CH₃)-1,3-dihydro-indol-2-on-6-yl |
| 1-218 | " | 1-allyl-5-F-1,3-dihydro-indol-2-on-6-yl |
| 1-219 | —(CH₂)₂CHFCH₂ | 6-F-1(2-propinyl)-3,4-dihydroquinolin-2(1H)-on-7-yl |
| 1-220 | " | 1-(2-propinyl)-5-F-benzo[d]-1,2,3-triazol-6-yl |

Key to Abbreviations (1) isomeric mixture of 4- and 5-substituted compound
(2) Ar=2-$R_2$-4-$R_3$-5-$R_4$-phenyl
(3) $Ar_1$=2-$R_2$-4-dihydro-benzo[b]-1,4-oxazin-3-on-6-yl
(4) $Ar_2$=3,4-dihydro-2H-quinoxalin-2-on-7-yl
(5) $Ar_3$=1 H-quinoxalin-2-on-7-yl
(6) $Ar_4$ Benzo[d]-1,3-thiazol-2(3H)-on-5-yl
(7) numbering convention stirred 16 hours longer at ambient temperature and is then washed with 140 ml of water, which contains 14 g of $KHCO_3$ and 2 g of $NaHSO_3$. Then the organic layer is separated, washed with water (150 ml), dried ($Na_2SO_4$) and evaporated in vacuo. The residue is chromatographed on a silica gel column.

Elution with ethyl acetate affords the title compound, which is homogenous by TLC (Rf=0.31 on silica gel with ethyl acetate-hexane 1:1).

In an analogous manner, the following compounds of formula (I) set forth in Table 2 are made.

TABLE 2

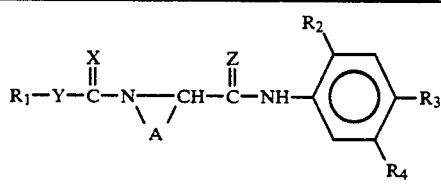

| Compd. | $R_1$ | A | X | Y | Z | $R_2$ | $R_3$ | $R_4$ | m.p. or $R_f$ on silica gel |
|---|---|---|---|---|---|---|---|---|---|
| 2-2 | phenyl | —$(CH_2)_2SO_2CH_2$— | O | O | O | F | Cl | $OCH_3$ | 74–76° |
| 2-3 | " | " | " | " | " | " | " | $OCH_2CH_3$ | 0,35 (ethyl acetate-hexane 1:1) |
| 2-4 | " | " | " | " | " | " | " | $OCH_2CH_2CH_3$ | 0.35 (ethyl acetate-hexane 1:1) |
| 2-5 | " | " | " | " | " | " | " | $OC_4H_9$-sec. | 0,38 (ethyl acetate-hexane 1:1) |
| 2-6 | " | " | " | " | " | " | " | $OC_5H_9$-cycl. | 0,37 (ethyl acetate-hexane 1:1) |
| 2-7 | " | " | " | " | " | " | " | $OCH_2C\equiv CH$ | 129–131° |
| 2-8 | " | " | " | " | " | " | " | $OCH(CH_3)C\equiv CH$ | 0,58 (ethyl acetate) |
| 2-9 | $CH_3$ | " | " | " | " | " | " | $OCH(CH_3)_2$ | 168–169° |
| 2-10 | " | " | " | " | " | " | " | $OCH(CH_3)C\equiv CH$ | $R_f$ = 0,47 (ethyl acetate) |

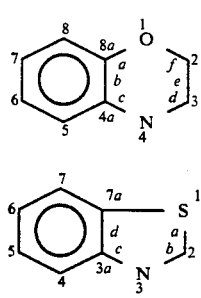

EXAMPLE 2-1

3[[(4-chloro-2-fluoro-5-isopropoxyphenyl)amino]carbonyl-4-thiomorpholine carboxylic acid phenyl ester-1,1 dioxide To 2.25 g (0.005 mol) of 3[[(4-chloro-2-fluoro-5-isopropoxyphenyl)-aminolcarbonyl-4-thiomorpholinecarboxylic acid-phenyl ester in 20 ml of methylene chloride ($CH_2Cl_2$) is added dropwise, without cooling a dried ($Na_2SO_4$) solution of 4 g of m-chloro-perbenzoic acid (55%/~0.013 mol) in 200 ml of $CH_2CH_2$. After the exothermic (28°) reaction has subsided, the reaction solution is

EXAMPLE 3-1

3[[(4-Chloro-2-fluoro-5-isopropoxyphenyl)azinolearbonyl]-4-thio morpholine carboxylic acid methyl ester-1-oxide To 13,3 g (0,034 mol) of 3[[(4-chloro-2-fluoro-5-isopropoxyphenyl)amino]carbonyl]-4-thiomorpholinecarboxylic acid-methyl ester in 150 ml of dry methylene chloride is added dropwise with stirring the dried ($Na_2SO_4$) solution of 7,25 g m-chloroperbenzoic acid (80 %; 0,034 mol) at such a rate, that the temperature does not rise above 5°.

After being kept at 50 for 20 hours, the reaction solution is washed with 500 ml of water which contains 50 g of $NaHCO_3$ and 5 g of $NaHSO_3$.

Then the organic layer is separated, washed with water (250 ml), dried ($Na_2SO_4$) and evaporated in vacuo.

The residue is chromatographed on a silica gel column.

Elution with ethyl acetate affords the title compound as a reddish amorphous solid which is homogeneous by TLC (Rf=0,07 on silica gel with ethyl acetate).

In an analogous manner, the following compounds set forth in Table 3 are made.

TABLE 3

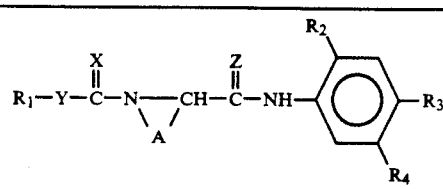

| Compd. No. | $R_1$ | A | X | Y | Z | $R_2$ | $R_3$ | $R_4$ | m.p. or Rf on silica gel |
|---|---|---|---|---|---|---|---|---|---|
| 3-2 | phenyl | —$(CH_2)_2SOCH_2$— | O | O | O | F | Cl | $OCH(CH_3)_2$ | 152–154° |
| 3-3 | " | " | " | " | " | " | " | $OCH_2C\equiv CH$ | 113–115° |
| 3-4 | " | " | " | " | " | " | " | $OCH(CH_3)C\equiv CH$ | $R_f$ = 0.13 (ethylacetate) |
| 3-5 | $CH_3$ | " | " | " | " | " | " | $OCH(CH_3)_2$ | $R_f$ = 0.08 (ethylacetate) |

INTERMEDIATES

EXAMPLE 4-1

Pipecolic acid 4-chloro-2-fluoro-5-isopropoxy anilide

To a suspension of 18.4 g (0.1 mol) pipecolic acid chloride hydrochloride in 400 ml methylenechloride are added 20.3 g (0.1 mol) 4-chloro-2-fluoro-5-isopropoxy aniline. After the exothermic (30° C.) reaction has subsided, 18 g NaHCO3 are added and the reaction mixture is stirred for 30 minutes at room temperature. 30 ml of water is added and stirring is continued for 1 hour. After the addition of 200 ml water the organic phase is separated, washed with 100 ml water, dried (MgSO4) and evaporated in vacuo. After treatment of the residue with pentane the compound is obtained in form of white crystals. Mp. 960° C.

In an analogous manner, the following compounds of formula (II) set forth in Table 4 are made.

TABLE 4

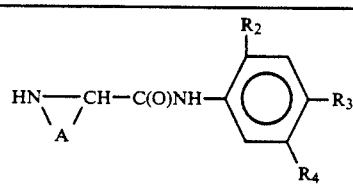

| Compound | HN—CH— \\A/ | $R_2$ | $R_3$ | $R_4$ | mp or $R_f$ |
|---|---|---|---|---|---|
| 4-2 | piperid-2-yl | F | Cl | H | 88° C. |
| 4-3 | " | " | " | $OCH_2CH_3$ | 88° C. |
| 4-4 | " | " | " | $OH_2CH_2CH_3$ | 89° C. |
| 4-5 | " | " | " | $OCH_3$ | 142° C. |
| 4-6 | " | " | " | $OCH(CH_3)_2$ | 94° C. |
| 4-7 | " | " | " | OCH—COOEt CH3 | $R_f$ = 0,1(Ether) |
| 4-8 | " | " | " | O—COOCH3 | 126° C. |
| 4-9 | " | H | " | $COOCH_2CH_3$ | 109° C. |
| 4-10 | 1,2,3,6-tetrahydro-pyridin-2-yl | F | " | $OCH(CH_3)_2$ | 71° C. |
| 4-11 | 1,4-thiomorpholin-3-yl | " | " | " | 84° C. |
| 4-12 | 2,3-dehydro-1,4-thiomorpholin-3-yl | " | " | " | |
| 4-13 | 3-F-piperidin-2-yl | F | Cl | $OCH(CH_3)_2$ | |
| 4-14 | 4-F-piperidin-2-yl | " | " | " | |
| 4-15 | 5-F-piperidin-2-yl | " | " | " | |
| 4-16 | 4,4-di-F-piperidin-2-yl | " | " | " | |
| 4-17 | 5,5-di-F-piperidin-2-yl | " | " | " | |
| 4-18 | 4-F-1,2,3,6-tetrahydro-pyridin-2-yl | " | " | " | |
| 4-19 | 5-F-1,2,3,6-tetrahydro-pyridin-2-yl | " | " | " | |
| 4-20 | 4,5-di-F-1,2,3,6-tetrahydro-pyridin-2-yl | F | Cl | $OCH(CH_3)_2$ | |
| 4-21 | 4,5-di-F-piperidin-2-yl | " | " | " | |
| 4-22 | 3,3-di-F-piperidin-2-yl | " | " | " | |

Biology

The herbicidal activity of the compounds of this application is demonstrated by experiments carried out for the pre-emergence and post-emergence control of a variety of weeds. Such weeds include Abutilon theophrasti, Amaranthus retroflux, Sinapis alba, Solanum nigrum, Bromus tectorum, Setaria viridis, Avena fatua, and Echinochloa crus-galli.

In preemergence testing, small plastic greenhouse pots filled with dry soil are seeded with the various weed seeds. Twenty-four hours or less after the seeding, the pots are sprayed with water until the soil is wet and the test compounds formulated as aqueous emulsions of acetone solutions containing emulsifiers are sprayed at the indicated concentrations emulsifiers are sprayed on the surface of the soil. After spraying, the soil containers are placed in the greenhouse and provided with supplementary heat as required and daily or more frequent watering. The plants are maintained under these conditions for a period of from 14 to 21 days, at which time the conditions of the plants and the degree of injury to the plants is rated.

In post-emergence testing, the compounds to be tested are formulated as aqueous emulsions and sprayed on the foliage of the various weed species that have attained a prescribed size. After spraying, the plants are placed in a greenhouse and watered daily or more frequently. Water is not applied to the foliage of the treated plants. The severity of the injury is determined 21 days after treatment and is rated.

In general, the compounds of this application demonstrate good activity against most of the weed varieties noted above. They are particularly active against Abutilon theophrasti and Solanum nigrum, in both pre- and post-emergence testing.

What is claimed is:

1. A compound of the formula (I)

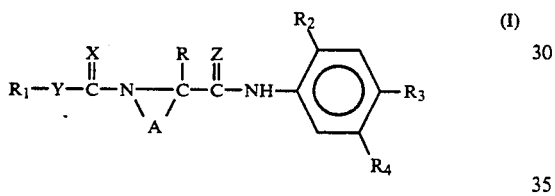

wherein
- R is H, $C_{1-3}$alkyl or $C_{2-3}$alkenyl optionally substituted by halo; or is $C_{2-3}$alkinyl;
- $R_1$ is phenyl$(C_{1-4}$alkyl$)_n$, wherein the phenyl group is optionally substituted by one or more groups selected from $-C(O)-O-C_{1-4}$alkyl, $C_{1-8}$alkyl, $C_{1-8}$haloalkyl, halo, nitro, cyano, $-SO_2C_{1-4}$alkyl, $SO_2NR_5R_5'$ and $S(O)NR_5R_5'$; or is $C_{5-8}$cycloalkenyl; $-N=R_6$; $C_{2-8}$alkenyl, $C_{1-8}$alkyl or $C_{3-5}$alkinyl optionally substituted with one or more halo; or is $C_{1-4}$alkyl$-SO_2-C_{1-4}$alkyl;
- $R_2$ is halo or hydrogen;
- $R_3$ is halo, cyano or $C_{1-4}$alkyl;
- $R_4$ is H; $NO_2$; $NH_2$; CN; $C_{1-8}$alkyl optionally substituted by CN; $C_{2-8}$alkenyl optionally substituted by CN; $C_{2-5}$alkinyl; $(C_{2-5}$alkoxycarbonyl$)-C_{1-4}$alkyl, whereby the carbon atom of the alkyl group alpha to the alkoxycarbonyl group may bear one more $C_{2-5}$alkoxcarbonyl groups or a cyano group; $(C_{2-5}$alkoxycarbonyl$)-C_{4}$alkoxy-$C_{1-4}$alkyl; $(C_{2-5}$alkoxycarbonyl$)-C_{1-4}$alkylamino-$C_{1-4}$alkyl; $(C_{2-5}$alkoxycarbonyl$)-C_{2-5}$alkenyl, whereby the alkenyl moiety is optionally substituted by halogen; $C_{1-4}$alkylthio-$C_{1-4}$alkyl; $C_{1-4}$alkylsulfonyl-$C_{1-4}$alkyl; $C_{1-4}$alkoxy-$C_{1-4}$alkoxy; $X(Alk)_mR_7$; $OCH(SR_8)-COOR_9$; $NR_{10}R_{11}$; $COOR_{12}$; $CONR_{13}R_{13}'$; $COR_{14}$ or $R_{15}$;
- or $R_3$ and $R_4$ join together with the phenyl ring to form a bicyclic ring containing nine to ten ring atoms, one to three of said ring atoms optionally being selected from oxygen, nitrogen and sulfur, and optionally being substituted with one or more groups selected from $C_{3-8}$alkinyl, $C_{1-8}$alkyl, halo, oxo, $C_{1-4}$alkylene-$R_{16}$, and $C_{2-8}$alkenyl;
- $R_5$ and $R_5$, independently are $C_{1-4}$alkyl;
- $R_6$ is $C_{2-8}$alkylidene;
- $R_7$ is H; $C_{1-4}$alkyl, $C_{2-5}$alkenyl $C_{2-5}$alkinyl, or $C_{3-8}$cycloalkyl, which hydrocarbyl is unsubstituted or substituted by one or more halogen or by CN; cyclopentanonyl; phenyl optionally substituted by $O-Alk'-COOR_8$; or is $C_{2-5}$alkanoyl; $C_{2-5}$alkoxycarbonyl; $C_{2-8}$(alkoxycarbonyl)$(C_{3-8}$cycloalkyloxy)-carbonyl, in which the alkoxy or cycloalkyloxy group is optionally substituted by one or more halo; $CONR_9R_8'$, $C(=NOR_8)-COOR_8'$, CN; $P(O)(OR_8)(OR_8')$ or $R_{15}$;
- $R_8$ and $R_8$, independently are $C_{1-4}$alkyl;
- $R_9$ is $C_{1-4}$alkyl optionally substituted by one or more halo;
- $R_{10}$ is H or $C_{1-4}$alkyl;
- $R_{11}$ is H; $C_{1-4}$alkyl, optionally substituted by $P(O)-(OR_8)(R_8')$; $C_{2-5}$alkanoyl; $C_{2-5}$alkoxycarbonyl; or $C_{2-5}$alkoxycarbonyl-$C_{1-4}$alkyl;
- $R_{12}$ is $N=(C_{2-8}$alkylidene); $C_{1-4}$alkyl optionally substituted by one or more groups selected from halo, $C_{1-4}$alkoxy, tri-$C_{1-4}$alkylsilyloxy, tri-$C_{1-4}$alkylsilyl, (tri-$C_{1-4}$alkylsilyloxy)-carbonyl, $C_{2-5}$alkoxycarbonyl, $P(O)(OR_8)(OR_8')$, $C_{2-5}$alkanoyl-oxy or by di$(C_{1-4}$alkylamino)-carbonyloxy in which both alkyl groups may be tied together to form a saturated 5 to 6 membered heteroring optionally containing one further heteroatom selected from O, S and N, and in which any further N-heteroatom present may, depending on the hydrogenation degree of the heteroring, bear a hydrogen or a $C_{1-4}$alkyl group;
- $R_{13}$ is H or $C_{1-4}$alkyl;
- $R_{13}$, is H, $C_{1-4}$alkyl optionally substituted by halo, $C_{1-4}$alkoxy, phenyl, CHO, $C_{2-5}$alkanoyl, $C_{1-4}$alkylsulfonyl, $(C_{2-5}$alkoxycarbonyl$)-C_{1-4}$alkyl or$(C_{2-5}$alkoxycarbonyl$)-C_{1-4}$alkoxy;
- or $R_{13}$ and $R_{13}$, together form a 4 to 6 membered heteroring optionally containing one or two further heteroatoms selected from O, S and N, whereby, depending on the hydrogenation degree of the heteroring, any further N-heteroatom may bear hydrogen or be substituted by $C_{1-4}$alkyl;
- $R_{14}$ is H or $C_{1-4}$alkyl;
- $R_{15}$ is a heterocyclic ring having 5 or 6 ring atoms, one to three of said ring atom being selected from oxygen, sulfur and nitrogen, which ring is optionally substituted with one or more $C_{1-4}$alkyl groups;
- $R_{16}$ is CN; $COOR_{12}$; $OC_{1-4}$alkyl; or is 4-tetrahydropyranyl, 2H-5,6-dihydro-thiin-3-yl, 2-pyridyl, 2-pyrazinyl, 1,2-oxazol-3-yl, or 1,2,4-oxdiazol-3-yl, each of which is optionally substituted with $C_{1-4}$alkyl;
- Alk and Alk' independently are $C_{1-4}$alkylene;
- n and m independently are 0 or 1;
- A is a $C_{3-4}$alkylene or straight chain substituted by one to three halogen; and
- X, Y and Z are independently selected from O and S.

2. A compound of formula (I) according to claim 1 wherein X, Y and Z are oxygen and R is H.

3. A compound of formula (I) according to claim 1 wherein A is straight chain butylene substituted by fluorine.

4. A compound of formula (I) according to claim 2 wherein $R_2$ is chlorine or fluorine and $R_3$ is CN, Br, Cl or methyl.

5. A compound of formula (I) according to claim 3 wherein $R_2$ is chlorine or fluorine and $R_3$ is CN, Br, Cl or methyl.

6. A compound of formula (I) according to claim 4 wherein $R_1$ is selected from the group consisting of phenyl optionally substituted with halogen, nitro or $CH_3OC(O)$—; $C_{1-4}$alkyl optionally substituted with one to four halogen atoms; $C_{2-4}$alkenyl; and $C_{2-3}$alkylidene=N—.

7. A compound of formula (I) according to claim 5 wherein $R_1$ is selected from the group consisting of phenyl optionally substituted with halogen, nitro or $CH_3OC(O)$—; $C_{1-4}$alkyl optionally substituted with one to four halogen atoms; $C_{2-4}$alkenyl; and $C_{2-3}$alkylidene=N—.

8. A compound of formula (I) according to claim 6 wherein $R_4$ is $O(Alk)_mR_7$, $COOR_{12}$ or $CONR_{13}R_{13'}$, $R_7$ is $C_{1-4}$alkyl, $C_{2-5}$alkenyl, $C_{2-5}$alkinyl or $C_{2-5}$alkoxycarbonyl, $R_{12}$ is $C_{1-4}$alkyl optionally substituted by halo, $R_{13}$ is H and $R_{13'}$ is $C_{1-4}$alkyl optionally substituted by halo.

9. A compound of formula (I) according to claim 7 wherein $R_4$ is $O(Alk)_mR_7$, $COOR_{12}$ or $CONR_{13}R_{13'}$, $R_7$ is $C_{1-4}$alkyl, $C_{2-5}$alkenyl, $C_{2-5}$alkinyl or $C_{2-5}$alkoxycarbonyl, $R_{12}$ is $C_{1-4}$alkyl optionally substituted by halo, $R_{13}$ is H and $R_{13'}$ is $C_{1-4}$alkyl optionally substituted by halo.

10. A herbicidal composition comprising a compound of formula (I) as defined in claim 1 and an agriculturally acceptable carrier.

11. A compound of the formula (II)

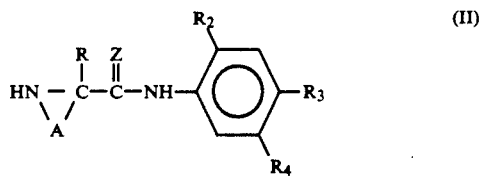

wherein $R$—$R_4$, A and Z are as defined in claim 1.

12. A method of combatting weeds which comprises applying to the weeds or their locus a herbicidally effective amount of the compound defined in claim 1.

* * * * *